United States Patent [19]

Xie et al.

[11] Patent Number: 6,133,339
[45] Date of Patent: Oct. 17, 2000

[54] DENTAL CEMENT FOR A TEMPORARY DENTAL PROSTHESIS OR APPLIANCE AND METHOD OF USE

[75] Inventors: Xiaoyi Xie, San Gabriel, Calif.; Duncan E. Waller, Ypsilanti, Mich.

[73] Assignee: Kerr Corporation, Orange, Calif.

[21] Appl. No.: 09/159,977

[22] Filed: Sep. 24, 1998

[51] Int. Cl.⁷ .............................. A61K 6/083; C08K 3/36
[52] U.S. Cl. .................... 523/116; 524/492; 524/493; 524/494; 524/559; 526/301
[58] Field of Search .................... 523/116; 524/492, 524/493, 494, 559; 526/301

[56] References Cited

U.S. PATENT DOCUMENTS

| | | | |
|---|---|---|---|
| 3,758,642 | 9/1973 | Logemann et al. | 524/297 |
| 4,016,124 | 4/1977 | Crisp et al. | 260/29.6 M |
| 4,362,510 | 12/1982 | Brauer et al. | 433/199 |
| 4,486,179 | 12/1984 | Brauer et al. | 433/199 |
| 4,591,384 | 5/1986 | Akahane et al. | 106/35 |
| 4,773,933 | 9/1988 | Futami et al. | 106/35 |
| 4,797,431 | 1/1989 | Billington et al. | 523/116 |
| 4,871,786 | 10/1989 | Aasen et al. | 523/116 |
| 4,872,936 | 10/1989 | Engelbrecht | 156/307.3 |
| 5,130,347 | 7/1992 | Mitra | 522/149 |
| 5,141,560 | 8/1992 | Combe et al. | 106/35 |
| 5,154,613 | 10/1992 | Cohen | 433/228.1 |
| 5,276,068 | 1/1994 | Waknine | 523/116 |
| 5,338,773 | 8/1994 | Lu et al. | 523/116 |
| 5,367,002 | 11/1994 | Huang et al. | 523/116 |
| 5,403,885 | 4/1995 | Voigt et al. | 524/731 |
| 5,453,456 | 9/1995 | Mitra et al. | 523/116 |
| 5,502,087 | 3/1996 | Tateosian et al. | 523/115 |
| 5,554,665 | 9/1996 | Tateosian et al. | 522/30 |
| 5,700,891 | 12/1997 | Huver et al. | 526/301 |
| 5,709,548 | 1/1998 | Oxman et al. | 523/116 |
| 5,861,445 | 1/1999 | Xu et al. | 523/116 |

FOREIGN PATENT DOCUMENTS

| | | |
|---|---|---|
| 0475239 | 1/1995 | European Pat. Off. . |

OTHER PUBLICATIONS

G.M. Brauer et al., *New Amine Accelerators for Composite Restorative Resins*, J. Dent Res 58(10): 1994–2000, Oct. 1979.

*Primary Examiner*—Andrew E. C. Merriam
*Attorney, Agent, or Firm*—Wood, Herron & Evans, LLP

[57] ABSTRACT

The invention describes a transparent, elastomeric dental cement composition suitable for temporary or provisional restorations that comprises: (a) at least one multifunctional oligomer or prepolymer as a binder; (b) at least one finely divided filler; and (c) at least one initiation system for polymerization. The cement has a high translucency which does not alter the color shade of a temporary prosthesis or appliance and great flexibility which allows the dentist to remove the temporary appliance easily and clean both the temporary appliance and the dental tissues easily. The invention also describes a method of using the transparent, elastomeric dental cement.

24 Claims, No Drawings

DENTAL CEMENT FOR A TEMPORARY DENTAL PROSTHESIS OR APPLIANCE AND METHOD OF USE

FIELD OF THE INVENTION

This invention relates to a dental cement and method of use for temporary or provisional restorations.

BACKGROUND OF THE INVENTION

Dental cements are used for adhering dental restoratives such as crowns, bridges, inlays and onlays to a tooth, providing a lining in a tooth cavity, fixing orthodontic appliances to the teeth and sealing root canals after endodontic treatment.

The dental profession has traditionally used durable cements for permanent restorations and temporary cements for temporary or provisional restorations. A durable cement is used for permanent restorations and is required to last for at least one year. A temporary cement can be used for up to three months as temporary or up to one year as provisional.

The commonly used dental cements for long term restorations are zinc phosphate cement, zinc poly(carboxylate) cement, glass ionomer cement and composite cement. These cements have good adhesion characteristics yet also exhibit high brittleness. The temporary dental cements are required to retain a temporary or provisional restoration for a specific period of time, but then allow the dentist to remove the restoration without having to apply undue pressure to the tooth or restoration. They are most commonly used for the period between the preparation and seating of a permanent restoration to ensure that the prepared tooth (teeth) is (are) healthy prior to permanent restoration. The traditional dental cement for temporary restorations is zinc oxide-eugenol cement, which has been used for over 100 years.

The zinc oxide-eugenol cements have demonstrated good biocompatibility, excellent sealing characteristics and effective bactericidal characteristics. They have found wide application in dentistry. Unfortunately, these materials have poor optical characteristics, being very opaque in appearance. These materials also inhibit free radical polymerization because of the presence of an electron-rich phenolic hydroxyl group in the eugenol molecule. Thus, acrylic resins, and to a lesser extent composites, in contact with a zinc oxide-eugenol cement do not polymerize completely. This incomplete cure results in polymer surface regions having reduced physical properties such as low surface hardness. Furthermore, zinc oxide-eugenol cements have a penetrating, long-lasting odor and lingering taste that can be unpleasant to many patients. In addition, incompletely hardened cements containing residual eugenol may produce irritation and cytotoxicity.

Crisp et al. in U.S. Pat. No. 4,016,124 disclose cements comprising acrylic acid/itaconic acid copolymers and fluoroaluminosilicate glass powder. Brauer et al. in U.S. Pat. No. 4,362,510 disclose cementitious dental compositions comprising a solid phase which includes a metal oxide or hydroxide of tin or a Group II metal and a liquid phase that includes a vanillic acid ester chelating compound. Brauer et al. in U.S. Pat. No. 4,486,179 disclose biocompatible cementitious dental compositions containing a syringic acid ester. Akahane et al. in U.S. Pat. No. 4,591,384 disclose a dental cement composition containing a water-soluble tannic acid derivative. Futami et al. in U.S. Pat. No. 4,773,933 disclose putty-form dental zinc oxide eugenol cement compositions. Billington et al. in U.S. Pat. No. 4,797,431 disclose radiopaque glass/poly(carboxylic acid) cement compositions. Engelbrecht in U.S. Pat. No. 4,872,936 discloses polymerizable cement mixtures containing acid monomers and reactive fillers. Mitra in U.S. Pat. No. 5,130,347 discloses a dental cement system containing a photocurable ionomer, reactive powder and water that undergoes both a self-curing reaction and a photo-curing reaction. Combe et al. in U.S. Pat. No. 5,141,560 disclose a dental cement comprising calcium or zinc oxide or hydroxide, a substituted aromatic compound and dry poly(carboxylic acid). Cohen et al. in U.S. Pat. No. 5,154,613 disclose dental cements for a temporary dental prosthesis or appliance containing a metal oxide, a metal hydroxide and an aqueous solution of a polycarboxylic acid. Lu et al. in U.S. Pat. No. 5,338,773 disclose further dental cement compositions and a method of use. These cement compositions include polymerizable acid reactive ethylenically unsaturated monomers, and a source of cations reactive therewith, to further crosslink the resulting polymer. Huang et al. in U.S. Pat. No. 5,367,002 disclose dental compositions formed by mixing a curable liquid composition containing polyalkenoic acid with a powder containing reactive fillers. Voigt et al. in U.S. Pat. No. 5,403,885 disclose a transparent dental bite-registration material based on addition-crosslinking polysiloxanes. Mitra et al. in U.S. Pat. No. 5,453,456 disclose a glass ionomer cement containing a silane-treated fluoroaluminosilicate glass. Huver et al. in U.S. Pat. No. 5,700,891 disclose a low-odor adhesive composition comprising (meth)acrylates containing urethane groups. Rheinberger et al. in European Patent No. 0 475 239 disclose dental compositions containing ethylenically unsaturated monomers and filler with a silica-metal oxide mixture and quartz or glass powder.

The prior art zinc phosphate cement, zinc poly(carboxylate) cement, glass ionomer cement and composite cement are strong, brittle and only suitable as permanent cements. There is no indication that these cements would be considered useful for temporary cementations because removal of the temporary prosthesis or appliance from the dental tissue is very difficult. The prior art zinc oxide-eugenol cements are very opaque, and alter the inherent, slightly translucent shade of temporary restorations. Furthermore, the prior art temporary cements are difficult to clean from both the temporary prosthesis or appliance and the dental tissue.

Problems typically arise after placing and curing in the tooth an opaque temporary cement for the cementing of temporary restorations such as inlays, onlays, crowns and bridges made of relatively transparent materials, e.g., porcelain or synthetic resin composites. The shade of the temporary is greatly affected by showing-through of the opaque temporary cement.

Accordingly, it would be desirable to provide an improved cement composition that is highly translucent, elastomeric and suitable for temporary or provisional restorations. It would also be desirable to provide a cement that retains a temporary or provisional restoration for a specific time period, then permits a dentist to easily remove the restoration. It would further be desirable to provide a cement that cleans up easily after it has set, and is easily removed from the temporary or provisional restoration and easily removed from the tooth tissue.

SUMMARY OF THE INVENTION

The present invention provides a highly translucent, elastomeric dental cement composition suitable for temporary or provisional restorations comprising at least one multifunctional oligomer or prepolymer as a binder; at least one finely divided filler; and at least one initiation system for polymerization.

The binder is advantageously an oligomeric or prepolymeric backbone to which is bonded polymerizable ethylenically unsaturated groups. The backbone may itself be a homopolymer or copolymer or may be polyurethane, polyester, polyamide, polyether, polysulfone or polyphosphazene. The binder also advantageously has a molecular weight of at least about 1,000.

The filler may be an organic filler, such as particulate polymers or copolymers or may be an inorganic filler, such as silicon dioxide or glass. The glass filler advantageously has an average particle size of less than about 200 microns.

The initiation system for polymerization is advantageously a redox system having either a peroxide initiator or a photoinitiator and an accelerator. The composition may be either a one-component system or a two-component system. In a paste/paste system, both pastes may contain an initiator with one paste also having an accelerator, to form a dual-cure composition. Advantageously, one of the pastes contains a photoinitiator and the other paste contains a chemical initiator, such as a peroxide.

The cement composition may optionally contain a polymerizable ethylenically unsaturated monomer, polymerization inhibitor, a non-polymerizable plasticizer and additives.

The present invention further encompasses a method of using the above-described elastomeric temporary or provisional dental cement which comprises the steps of mixing the cement composition; applying the cement composition to a temporary or provisional prosthesis or appliance; seating the prosthesis or appliance over a dentition in the patient's mouth; and self-curing the cement composition and/or curing the cement composition by irradiation from a light curing apparatus.

These and other objects and advantages of the present invention shall become more apparent from the accompanying description of the preferred embodiments of the invention and the examples.

DETAILED DESCRIPTION

The temporary cement of the present invention is characterized by high translucency, which does not alter the inherent shade of temporary or provisional restorations, and by high flexibility, which allows the dentist to remove the temporary restorations easily and clean both the temporary and the prepared tooth/teeth easily.

The temporary cement composition of the present invention comprises at least one multifunctional oligomer or prepolymer as a binder; at least one finely divided filler; and at least one initiation system for polymerization of the binder.

The temporary cement of the present invention is preferably derived from a catalyst paste and a base paste. The two pastes are intimately mixed together in a paste/paste system, the hardening of which is initiated by means of a redox polymerization initiator system, wherein the catalyst paste contains a polymerization initiator and the base paste contains a polymerization accelerator.

Alternatively, the temporary cement of the invention may comprise a single paste component the hardening of which is initiated by means of a photoinitiator for photopolymerization.

The translucent appearance of the cement of this invention is obtained by using materials having similar refractive indices. For a filled cement composition, the refractive index of the liquid matrix (the binder components) must match closely to the refractive index of the filler components. Preferably, the refractive index of the major components in the liquid matrix is slightly lower, in an amount of between about 0.005 and about 0.02, than that of the filler components because the polymerized matrix generally has a somewhat higher refractive index than the liquid matrix. Thus the refractive index of the polymer matrix matches or is very similar to that of the filler when the cement is completely cured. The resulting cement preferably has a translucency of about 30% or greater at a thickness of 1 mm.

The elastomeric feature of the cement of the present invention is obtained by polymerization of a multifunctional oligomer or prepolymer. Multifunctional oligomers or prepolymers useful in accordance with the invention include polyester and polyether (meth)acrylates, urethane (meth)acrylates, and polygylcol (meth)acrylate(s), all of which are capable of addition polymerization. The term "(meth)acrylate" herein means either methacrylate or acrylate. In general, the preferred reactive functionalities that serve as active sites for the polymerization are at least two in the present invention. The preferred reactive functional groups are acrylic and/or methacrylic groups. It is advantageous for the oligomers and the prepolymers to have a molecular weight of at least about 1000, although preferably no greater than about 100,000 and preferably no greater than about 30,000. Furthermore, mixtures of multifunctional monomers and/or oligomers are useful in compositions of the present invention.

Examples of urethane polyacrylate prepolymers that are preferred for use in the present invention include: (1) the adduct of 1 mole of polyester diol or polyether diol with 2 moles of hexamethylene diisocyanate or another difunctional isocyanate to which is added 2 moles of hydroxyethyl or hydroxypropyl (meth)acrylate; (2) the adduct of 1 mole of polyester diol or polyether diol and 2 moles of isocyanato ethylmethacrylate; and (3) the adduct of 1 mole of polyester or plyether diisocyanate and 2 moles of hydroxyethyl or hydroxypropyl(meth)acrylate.

Suitable commercially available oligomeric or polymeric resins as the binder component of the present invention include acrylated urethanes such as SARTOMER CN966, CN981, CN972, CN973 (Sartomer Company, Inc., West Chester, Pa.), and EBECRYL 230, 244, 264, 270, 4827, 6700, 8301, 8402, 8804 (UCB Chemicals Corporation Louisville, Ky.), as well as acrylated polyesters such as EBECRYL 657, 830, 1657, 1701, 2870 (UCB Chemicals Corporation). Mixtures of monomers, oligomers or prepolymers may be used if desired.

Additional exemplary prepolymers for use in the present invention include polyorganosiloxane di(meth)acrylates and polycarbonate urethane di(meth)acrylates.

Mixtures of the above-identified exemplary prepolymers and other similar oligomers may be used as the sole polymerizable ingredient. Alternatively, the fluid polymerizable composition may include diluent comonomers, such as lower viscosity diluent monomers and oligomers, including polyethylene glycol di(meth)acrylate, butylene glycol di(meth)acrylate and the like.

The cement composition of the present invention may include polymerizable ethylenically unsaturated monomers such as ethylene glycol di(meth)acrylate, diethylene glycol di(meth)acrylate, triethylene glycol di(meth)acrylate, tetraethylene glycol di(meth)acrylate, neopentyl glycol di(meth)acrylate, 1,3-butanediol di(meth)acrylate, 1,6-hexanediol di(meth)acrylate, propylene glycol di(meth)acrylate, dipropylene glycol di(meth)acrylate, tripropylene glycol di(meth)acrylate, trimethylolpropane tri(meth)acrylate, urethane di(meth)acrylate, 2,2-bis(4-(2-hydroxy-3-acryloyloxypropoxy) phenyl)propane, 2,2-bis(4-(2-hydroxy-3-methacryloyloxypropoxy) phenyl)propane (Bis-GMA), 2,2-bis(4-(acryloyloxy-ethoxy) phenyl)propane, 2,2-bis(4-(methacryloyloxy-ethoxy)phenyl)propane, and the like. The function of the ethylenically unsaturated monomers is twofold. They may be used as diluents to adjust the viscosity of the cement composition. They may also improve the polymer matrix structure and increase the surface hardness of the cured material.

Polymerizable ethylenically unsaturated monomers useful in accordance with the present invention also include monofunctional monomers such as cyclohexyl methacrylate, benzyl methacrylate, t-butyl methacrylate, n-butyl methacrylate, isobutyl methacrylate, and 2-ethylhexyl methacrylate.

An especially advantageous mixture results when hydroxy functional monomers that contain one or more polymerizable ethylenically unsaturated groups are added to the cement composition. This addition serves to increase the hydrophilic characteristics of the cement and to enhance the adhesion of the cement to the tooth surface. Appropriate for this purpose are hydroxyalkyl methacrylates, such as hydroxyethyl methacrylate and hydroxypropyl methacrylate, that also contain hydroxyl groups, and dimethacrylate compounds, such as glycerol dimethacrylate, that contain hydroxyl groups. The preferred hydroxy-group-containing compound for use in the present invention is hydroxyethyl methacrylate. The function of the hydroxyethyl methacrylate is to increase the bonding strength of the cement composition of the invention to the tooth. A suitable amount of the hydroxyethyl methacrylate in the composition of the present invention is in the range of up to about 40% by weight.

The fillers in the composition of the present invention are chosen primarily for viscosity modification, but they may also be used to influence the adhesion properties of the cement. The fillers useful in the paste compositions of the present invention include organic and inorganic fillers. Organic fillers are particulate polymers or copolymers. Inorganic fillers are silicon dioxide and glasses. A preferred silicon dioxide is submicron amorphous fumed silica, preferably treated with a silane or polymer to improve hydrophobicity. Its thixotropic characteristics greatly improve the stackability of the composition and allow easy extrusion through a syringe. Preferably, a suitable amount of submicron fumed silica is in the range of about 1% to about 25% by weight. Suitable glass fillers include borosilicate glass, barium glass, strontium glass, yttrium glass, zirconium glass, lanthanum glass, and the like. A preferred glass filler is borosilicate glass. Borosilicate glass exhibits substantially the same refractive index as that of the urethane (meth)acrylate monomeric matrix in which it is dispersed. Preferably, the glass filler has a particle size of less than about 200 microns, and more preferably in the range of about 0.1 to about 10 microns. Further, the filler is preferably treated with a silane such as gamma-methacryloxy propyl trimethoxy silane (trade name A-174 manufactured by Union Carbide, Danbury, Conn.) to improve bonding between the filler and the polymer matrix. Other silanes can also be substituted for this purpose. The glass filler is preferably present in the composition in an amount of up to about 60% by weight.

Polymerization initiators may be chosen from known organic peroxides such as dibenzoyl peroxide, di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide, cumene hydroperoxide, and the like. A suitable and preferred peroxide is dibenzoyl peroxide. A suitable amount of the dibenzoyl peroxide present in the composition of the present invention is in the range of about 0.1% to about 2% by weight.

The cement composition of the present invention optionally includes a polymerization inhibitor such as butylated hydroxytoluene, hydroquinone, hydroquinone monomethyl ether, benzoquinone, chloranil, phenol, and the like. A preferred polymerization inhibitor is butylated hydroxytoluene. The inhibitor is used to scavenge small amounts of free radicals during storage and to improve the shelf stability of the cement. More than one inhibitor may be used in the cement composition of the invention. For example, in a two paste system, both the catalyst paste and the base paste may contain a polymerization inhibitor. The polymerization inhibitor is preferably present in an amount of about 0.001% to about 2% by weight, more preferably about 0.01% to about 0.5%.

Polymerization accelerators must be used in combination with the peroxide initiator to allow rapid polymerization of the monomers at room temperature. One skilled in the art will appreciate that tertiary amines are generally preferred for use in dental restoratives, as described in an article by G. M. Brauer et al. in 58 Journal of Dental Research 1994–2000 (1979), the entirety of which is incorporated herein by reference. One skilled in the art will also appreciate that known tertiary amines or newly synthesized tertiary amines may be used. Typical tertiary amines include triethanol amine, N,N,3,5-tetramethyl aniline, 4-(dimethylamino)-phenethyl alcohol, dimethyl aminobenzoic acid ester, dimethyl-p-toluidine, dihydroxyethyl-p-toluidine, and the like. A preferred amine accelerator for use in the present invention is dihydroxyethyl-p-toluidine. A suitable amount of dihydroxyethyl-p-toluidine is in the range of about 0.01% to about 5% by weight.

In addition, the cement composition may optionally include one or more non-polymerizable plasticizers in an amount up to about 40% by weight to increase flow properties of the cement and to improve flexibility of the cured cement. As a result, when a temporary restoration is subsequently removed from the dental tissue, as described in more detail hereinbelow, residual cement remaining on the tooth surface may be quickly and easily removed. A non-polymerizable plasticizer may be chosen from saturated or inert liquid organic compounds including alkylphthalates, liquid paraffins and low-molecular-weight polyglycols. Examples are diethyl phthalate, dibutyl phthalate, octyl benzyl phthalate, mineral oil, poly(ethylene glycol)-Mn 200~400, poly(propylene glycol)-Mn 400~4000, and the like, where Mn refers to the number average molecular weight. A preferred non-polymerizable plasticizer is dibutyl phthalate.

In one embodiment of the present invention, a photoinitiator and promoter (also referred to as a photopolymerization accelerator) is added to the cement composition to make it light-curable. In this embodiment, it is necessary that the cement composition be stored in an opaque container, typically a black container. Typical photoinitiators include benzophenone, acetophenone, thioxanethen-9-one, 9-fluorenone, anthraquinone, 4'-methoxyacetophenone, diethoxyacetophenone and the diketones, such as biacetyl, 2,3-pentanedione, benzil, 4,4'-methoxybenzil, 4,4'-oxidibenzil and camphorquinone. Camphorquinone is the most commonly used photoinitiator for dental materials. It absorbs mostly in the visible light spectrum between 400 and 500 nanometers. Formulations with the camphorquinone initiator cure readily with visible radiation. Photoinitiators are preferably used in concentrations between about 0.001% and 10% by weight of the polymerizable resin, and more preferably between about 0.01% and about 5%.

The photopolymerization promoter may be chosen from the same list of tertiary amines listed for use as polymerization accelerators in combination with a peroxide for self-curing polymerization. Tertiary amines with additional functional groups are also employed such as 4,4'-bis (dimethylamino) benzophenone, N-methyldiethanolamine, 4-dimethylaminobenzoate, dimethylaminobenzaldehyde, dimethylaminoethylmethacrylate and dimethylaminoethylacrylate. Alternatively, the same tertiary amine may be utilized as polymerization accelerator and photopolymerization promoter in the composition of the present invention. The tertiary amines are preferably present in an amount of about 0.001% to about 10% by weight of the polymerizable resin, and more preferably about 0.01% to about 5%.

For aesthetic or other purposes, the cement compositions of the present invention may include small quantities of additives such as pigments, dyes, opalescent agents, fluorescent agents, ultraviolet stabilizers, anti-oxidants, antimicrobials and the like, provided that they do not substantially affect cure.

In a preferred embodiment of the present invention, the cement composition is present in a paste form which may be achieved by using standard compounding techniques. The liquid ingredients containing an appropriate initiator and/or accelerator are mixed with fillers in a planetary mixer to form homogeneous pastes. The resulting pastes may be passed through a three roll porcelain mill, if desired, to ensure homogeneity. The resulting pastes are then deaerated in a planetary mixer under vacuum to remove air bubbles.

In a preferred embodiment of the invention the cement composition is present in two paste components, catalyst paste and base paste, which are stored in a non-contact state and mixed together just prior to use. Preferably the paste compositions mixed in accordance with the present invention have substantially the same viscosity. The catalyst paste and base paste compositions are packaged in appropriate packaging which permits easy dispensing, such as in syringes. A polymerizing cement is produced by mixing the catalyst paste and base paste together, typically in a static mixer. Preferably the catalyst paste and base paste are mixed in a 1:1 ratio. The polymerization catalyst is activated when the catalyst and base pastes are mixed. The mixed paste starts polymerizing in less than 4 minutes from the beginning of mixing. The viscosity of the mixed paste increases gradually. Within less than 8 minutes from the beginning of mixing, the polymerizing paste is hardened.

Alternatively, a photoinitiator may be added to either the catalyst paste or the base paste and a photopolymerization promoter may be added to the base paste, thus producing a two-component dual-cure cement. In this embodiment, the polymerizing cement is produced by mixing the catalyst paste and base paste thereby activating the peroxide initiator and accelerator/promotor. The cement is further cured by irradiating light from a light source to activate the photoinitiator and accelerator/promotor.

In another embodiment of the invention, the cement composition is a light-curable one-paste component containing at least one photoinitiator and at least one photopolymerization promoter and can be used without mixing. For the light-cure or dual-cure cements, it is necessary that the cement composition be packaged in a light-proof syringe, typically a black syringe.

After preparing and mixing the temporary cement composition of the invention, the cement is applied to a dental prosthesis or appliance (such as a inlay, onlay, crown or bridge). Typically, a small amount of cement is added or applied to the inner surface of the prosthesis or appliance, the surface which must be attached to the dental tissue. After the prosthesis or appliance is positioned, the patient is instructed to "bite down" on the prosthesis or appliance, so that the exposed dental tissue makes intimate contact with the inner surface of the prosthesis or appliance (where the cement has been applied). This causes the cement to spread along the region of contact between the dental tissue and the prosthesis or appliance. Any excess cement which has exuded from the contact area may be easily scraped away. The cement composition starts polymerizing in less than about 4 minutes, preferably less than about 2 minutes from the beginning of mixing. Within less than about 8 minutes, preferably less than about 4 minutes from the beginning of mixing, the cement composition is hardened.

When it is desired to remove the temporary prosthesis or appliance from the mouth of the patient, a dentist will utilize a dental instrument for detaching the prosthesis or appliance from the dental tissue. Suitable instruments include an explorer, a probe or a crown remover.

The temporary cement in accordance with the invention is an elastomeric material which does not strongly adhere to dental tissues. Thus, it is easily removed from the dental tissues. More particularly, the cement has stronger adhesion to the prosthesis or appliance, therefore, when the dentist removes the temporary prosthesis or appliance from the mouth of the patient, the temporary cement in accordance with the present invention is separated from the dental tissues and remains on the surface of the prosthesis or appliance. Thus it leaves clean surfaces on the dental tissues.

Many times, a dentist may want to re-use the temporary prosthesis or appliance since the permanent prosthesis or appliance may not be ready and the cost and effort to prepare a new temporary may be substantial. However, before re-using the temporary prosthesis or appliance, it is necessary to remove residual cement remaining thereon, particularly along undercuts in the prosthesis or appliance. This may be achieved by using a dental instrument such as an explorer, a probe or a scaler to detach the elastomeric cement and easily remove it from the prosthesis or appliance. The elastomeric characteristics of the cement composition of the invention reduce the adhesion to dental tissues and prosthesis or appliance. As a result, a temporary prosthesis or appliance can be easily removed from dental tissue, and residual cement remaining on the tooth surface and on the temporary prosthesis or appliance surface can be quickly and easily removed.

The following examples further illustrate the various embodiments of the present invention. Neither these examples nor any of the foregoing disclosure should be construed as limiting in any way the scope of the present invention. Unless otherwise indicated, all parts and percentages are by weight.

EXAMPLE 1

Synthesis of Urethane Dimethacrylate Prepolymer 37.5 parts of plasticizer alkyl benzyl phthalate (Santicizer 261, Solutia Inc., St. Louis, Mo.), 50.5 parts of diethyleneadipate polyesterdiol (Rucoflex S-1011-55, MW 2000, Ruco Polymer Corp., Hicksville, N.Y.), 4.9 parts of hydroxypropyl methacrylate (Aldrich Chemical Co., Milwaukee, Wis.) and 0.04 parts of dibutyltindilaurate catalyst are placed in a three necked flask fitted with stirrer, dropping funnel, thermometer and drying tube and stirred thoroughly. Add 7.1 parts of 1,6-hexanediisocyanate via the dropping funnel at such a rate that temperature does not exceed 40° C. Cool with cold tap water if necessary. Monitor reaction progress with infrared spectrophotometer until isocyanate peak is no longer detectable.

EXAMPLE 2

A two-paste dual-cure cement composition of the present invention is listed in the following table:

TABLE 1

|  | WT. % | Refractive Index @ 25° C. |
|---|---|---|
| CATALYST PASTE |  |  |
| Urethane dimethacrylate prepolymer from EXAMPLE 1 | 63.6 | 1.497 |
| Dibenzoyl peroxide | 0.4 |  |
| Butylated hydroxytoluene | 0.00025 |  |
| Fumed silica | 4.0 | 1.460 |
| Borosilicate glass filler, silanized | 32.0 | 1.480 |
| BASE PASTE |  |  |
| Urethane dimethacrylate prepolymer from EXAMPLE 1 | 63.0 | 1.497 |
| Butyl p-Hydroxy Benzoate (anti-microbial) | 0.58 |  |
| N,N-Dihydroxyethyl-p-toluidine | 0.74 |  |
| Butylated hydroxytoluene | 0.00025 |  |
| Camphorquinone | 0.2 |  |
| Dimethylaminoethylmethacrylate | 0.5 |  |
| Fumed silica | 4.0 | 1.460 |
| Borosilicate glass filler, silanized | 31.0 | 1.480 |

Both catalyst paste and base paste are separately formed by mixing the ingredients in a planetary mixer. The resulting pastes are passed through a three roll mill and then deaerated under vacuum in the planetary mixer separately to ensure homogeneity. Because this is a dual-cure cement, the base paste must be stored in black syringes to extend the shelf life.

The two pastes are preferably mixed in equal quantities just before application. The polymerizing cement composition is either cured automatically or cured by a dental curing light. When auto-cured, the cement has a gel time of about 2 minutes and a set time of about 4 minutes. The Shore A hardness was 88. The translucency at a thickness of about 1.03 mm was about 52%. When light-cured for 10 seconds, the material cured to a depth of about 6.89 mm. The gel time was measured as the time it takes from the initial mixing of the pastes for the material to no longer peak up from the surface when probed by a hand-held sharp instrument. The set time was measured as the period of time during which the hand-held probe is capable of penetrating the surface of the material. The translucency is measured as the percentage of light transmitted through the testing sample (25 mm×1 mm disk) using a calorimeter model xL10 (Gardner Company, Inc., Silver Spring, Md.) in a transmission mode as per American Dental Association Specification #27.

EXAMPLE 3

A single-paste light-curable cement composition of the present invention is listed in the following table:

TABLE 2

| PASTE | WT. % | Refractive Index @ 25° C. |
|---|---|---|
| Ebecryl 270 Urethane diacrylate Oligomer | 51.53 | 1.475 |
| 2-Hydroxyethyl methacrylate | 12.0 | 1.450 |
| Butyl p-Hydroxy Benzoate (anti-microbial) | 0.3 |  |
| 4-(Dimethylamino)phenethyl alcohol | 1.0 |  |
| Butylated hydroxytoluene | 0.02 |  |
| Camphorquinone | 0.15 |  |
| Fumed silica | 3.0 | 1.460 |
| Borosilicate glass filler, silanized | 32.0 | 1.480 |

The paste is formed by mixing the ingredients in a planetary mixer. The resulting paste is passed through a three roll mill and then deaerated under vacuum in the planetary mixer to ensure homogeneity. Because this is a light-cure cement, the paste must be stored in black syringes to extend the shelf life.

The paste cement composition is cured by a dental curing light. When exposed to a light source for 10 seconds, the material cured to a depth of about 7.79 mm. The Shore A hardness was 91. The translucency at a thickness of about 1.06 mm was about 62%.

EXAMPLE 4

A catalyst paste composition of a two-paste dual-cure cement of the present invention is listed in the following table:

TABLE 3

| CATALYST PASTE | WT. % | Refractive Index @ 25° C. |
|---|---|---|
| Ebecryl 270 Urethane diacrylate Oligomer | 45.84 | 1.475 |
| Dibutyl phthalate | 18.0 | 1.491 |
| Dibenzoyl peroxide | 0.8 |  |
| Butylated hydroxytoluene | 0.06 |  |
| Butyl p-Hydroxy Benzoate (anti-microbial) | 0.3 |  |
| Fumed silica | 3.0 | 1.460 |
| Borosilicate glass filler, silanized | 32.0 | 1.480 |

The base paste composition is the same as that listed in Table 2 of EXAMPLE 3.

Both the catalyst paste and the base paste are separately formed by mixing the ingredients in a planetary mixer. The resulting pastes are passed through a three roll mill and then deaerated under vacuum in the planetary mixer separately to ensure homogeneity. Because this is a dual-cure cement, the base paste must be stored in black syringes to extend the shelf life.

The two pastes are preferably mixed together in equal quantities just before application. The polymerizing cement composition is either cured automatically or cured by a dental curing light. When auto-cured, the cement has a gel time of about 1 ¾ minutes and a set time of about 3 ¼ minutes. The Shore A hardness was 98. The translucency at a thickness of about 1.05 mm was about 60%. When light-cured for 10 seconds, the material cured to a depth of >8.0 mm.

It should be understood that while the present invention has been described in detail with respect to specific embodiments thereof, it should not be considered limited to such embodiments but may be used in other ways without departure from the essential features thereof.

What is claimed is:

1. An elastomeric temporary dental cement composition comprising:
   (a) a resinous mixture comprising free-radically polymerizable resin, the resin including at least one binder selected from the group consisting of a multifunctional oligomer and a multifunctional prepolymer said binder having an effective molecular weight to impart an elastomeric feature, and said resinous mixture being liquid at ambient temperature;
   (b) at least one finely divided filler, wherein the refractive index of the liquid matrix is within about +/−0.02 of the refractive index of the filler; and
   (c) at least one initiation system for polymerization, wherein, after polymerization, the cured elastomeric dental cement has a translucency of at least about 30% at a thickness of 1 mm.

2. The cement composition of claim 1, wherein the binder comprises a backbone selected from the group consisting of: an oligomeric backbone and a prepolymeric backbone, and at least one polymerizable ethylenically unsaturated group bonded to the backbone.

3. The cement composition of claim 2, wherein the backbone is selected from the group consisting of: homopolymers and copolymers.

4. The cement composition of claim 2, wherein the backbone is selected from the group consisting of: polyurethane, polyester, polyamide, polyether, polysulfone, and polyphosphazene.

5. The cement composition of claim 1, wherein the filler is an organic filler selected from the group consisting of: particulate polymers and particulate copolymers.

6. The cement composition of claim 1, wherein the filler is an inorganic filler selected from the group consisting of silicon dioxide and glass.

7. The cement composition of claim 6, wherein the glass is selected from the group consisting of: borosilicate glass, barium glass, strontium glass, yttrium glass, zirconium glass, and lanthanum glass.

8. The cement composition of claim 7, wherein the filler has an average particle size of less than about 200 microns.

9. The cement composition of claim 1, wherein initiation system for polymerization is a redox system that comprises at least one peroxide as a polymerization initiator and at least one tertiary amine as a polymerization accelerator.

10. The cement composition of claim 9, wherein the polymerization initiator is dibenzoyl peroxide.

11. The cement composition of claim 10, wherein the polymerization accelerator is dihydroxyethyl-p-toluidine.

12. The cement composition of claim 1, further comprising at least one polymerization inhibitor.

13. The cement composition of claim 12, wherein the polymerization inhibitor is butylated hydroxytoluene.

14. The cement composition of claim 1, further comprising at least one ethylenically unsaturated monomer.

15. The cement composition of claim 1, further comprising a non-polymerizable plasticizer.

16. The cement composition of claim 15, wherein the non-polymerizable plasticizer is dibutyl phthalate.

17. The cement composition of claim 1, wherein the initiation system for polymerization comprises a mixture of an α-diketone as a photoinitiator and a tertiary amine as a photopolymerization accelerator.

18. The cement composition of claim 17, wherein the photoinitiator is camphorquinone.

19. The cement composition of claim 17, wherein the photopolymerization accelerator is 4-(Dimethylamino) phenethyl alcohol.

20. A method of using an elastomeric temporary dental cement composition comprising the steps of:
   providing a cement composition comprising:
      (a) a resinous mixture comprising free-radically polymerizable resin, the resin including at least one binder selected from the group consisting of: a multifunctional oligomer and a multifunctional prepolymer, said binder having an effective molecular weight to impart an elastomeric feature, and said resinous mixture being liquid at ambient temperature;
      (b) at least one finely divided filler, wherein the refractive index of the liquid matrix is within about +/−0.02 of the refractive index of the filler, and
      (c) at least one initiation system for polymerization;
   mixing the cement composition;
   applying the cement composition to a temporary prosthesis;
   optionally applying the cement composition to hard dental tissue;
   seating the temporary prosthesis onto the hard dental tissue;
   curing the cement composition, wherein the cured elastomeric dental cement has a translucency of at least about 30% at a thickness of 1 mm; and
   removing the temporary prosthesis within 3 months of seating the temporary prosthesis.

21. The method of claim 20, wherein the cement composition is further cured by irradiation from a light curing apparatus.

22. A method of using an elastomeric temporary dental cement composition comprising the steps of:
   providing a cement composition comprising:
      (a) a resinous mixture comprising free-radically polymerizable resin, the resin including at least one binder selected from the group consisting of: a multifunctional oligomer and a multifunctional prepolymer, said binder having an effective molecular weight to impart an elastomeric feature, and said resinous mixture being liquid at ambient temperature;
      (b) at least one finely divided filler, wherein the refractive index of the liquid matrix is within about +/−0.02 of the refractive index of the filler, and
      (c) at least one initiation system for polymerization;
   mixing the cement composition;
   applying the cement composition to a provisional appliance;
   optionally applying the cement composition to hard dental tissue;
   seating the provisional appliance onto the hard dental tissue;
   curing the cement composition, wherein, the cured elastomeric dental cement has a translucency of at least about 30% at a thickness of 1 mm; and
   removing the provisional appliance within 1 year of seating the provisional appliance.

23. The method of claim 22, wherein the cement composition is further cured by irradiation from a light curing apparatus.

24. A temporary dental cement composition comprised of a mixture of a catalyst paste and a base paste, wherein the catalyst paste is comprised of:
   (a) a resinous mixture comprising free-radically polymerizable resin, the resin including at least one binder selected from the group consisting of: a multifunctional oligomer and a multifunctional prepolymer, said binder having an effective molecular weight to impart an elastomeric feature, and said resinous mixture being liquid at ambient temperature;

(b) at least one finely divided filler, wherein the refractive index of the liquid matrix is within about +/−0.02 of the refractive index of the filler, and (c) at least one polymerization initiator; and wherein the base paste is comprised of:

(a) a resinous mixture comprising free-radically polymerizable resin, the resin including at least one binder selected from the group consisting of: a multifunctional oligomer and a multifunctional prepolymer, said binder having an effective molecular weight to impart an elastomeric feature, and said resinous mixture being liquid at ambient temperature;

(b) at least one finely divided filler, wherein the refractive index of the liquid matrix is within about +/−0.02 of the refractive index of the filler, and (c) at least one polymerization accelerator, wherein, after polymerization, the cured elastomeric dental cement mixture has a translucency of at least about 30% at a thickness of 1 mm.

* * * * *